(12) United States Patent
Onogi et al.

(10) Patent No.: US 9,310,331 B2
(45) Date of Patent: Apr. 12, 2016

(54) NO$_x$ DETECTION APPARATUS AND NO$_x$ SENSOR SYSTEM

(71) Applicant: NGK SPARK PLUG CO., LTD., Nagoya, Aichi (JP)

(72) Inventors: Hirotaka Onogi, Kakamigahara (JP); Yuichi Ishida, Nagoya (JP); Satoshi Teramoto, Nissin (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 285 days.

(21) Appl. No.: 14/080,444

(22) Filed: Nov. 14, 2013

(65) Prior Publication Data

US 2014/0131200 A1 May 15, 2014

(30) Foreign Application Priority Data

Nov. 15, 2012 (JP) ................... 2012-251344

(51) Int. Cl.
*G01N 27/407* (2006.01)
*G01N 33/00* (2006.01)

(52) U.S. Cl.
CPC .......... *G01N 27/407* (2013.01); *G01N 33/0037* (2013.01)

(58) Field of Classification Search
CPC . G01M 15/10; G01M 15/102; G01M 15/104; G01N 1/2252; G01N 27/404–27/407; G01N 27/409; G01N 27/419; G01N 27/41; F01N 2560/00–2560/20; F01N 2550/00–2550/24; F01N 3/10; F01N 11/00
See application file for complete search history.

(56) References Cited

U.S. PATENT DOCUMENTS

| 2004/0138825 A1 | 7/2004 | Kawase et al. |
| 2006/0231422 A1 | 10/2006 | Rhodes et al. |
| 2009/0223820 A1* | 9/2009 | Ishiguro ............... G01N 27/419 204/424 |

FOREIGN PATENT DOCUMENTS

| JP | 2000-314718 A | 11/2000 |
| JP | 2004-132841 A | 4/2004 |
| JP | 2004-239632 A | 8/2004 |
| JP | 2009-210450 A | 9/2009 |

OTHER PUBLICATIONS

JPO, Notification of Reason for Rejection issued in corresponding Japanese Application No. 2012-251344, dispatched Feb. 24, 2015.

* cited by examiner

*Primary Examiner* — Jennifer Dieterle
(74) *Attorney, Agent, or Firm* — Stites & Harbison, PLLC; Jeffrey A. Haeberlin; James R. Hayne

(57) ABSTRACT

An NO$_x$ detection apparatus does not always perform correction processing, but it determines whether to perform the correction processing on the basis of the result of a determination of whether a first No$_x$ concentration is higher than a predetermined specific concentration. The first NO$_x$ concentration NO$_{xpo}$ calculated from a second pumping current Ip2 which changes with the actual NO$_x$ concentration. Therefore, the NO$_x$ detection apparatus can determine whether to correct the first NO$_x$ concentration NO$_{xpo}$ in accordance with the actual NO$_x$ concentration. Accordingly, the NO$_x$ detection apparatus can suppress a decrease in gas detection accuracy even in the case where the gas detection value based on the sensor output involves an error in a specific concentration range (concentration range of 90 ppm or higher).

6 Claims, 10 Drawing Sheets

| Rank | NOx pressure correction coefficient ($K_1$) |
|---|---|
| 0 | 10 |
| 1 | 14 |
| 2 | 18 |
| 3 | 22 |
| 4 | 26 |
| 5 | 30 |
| 6 | 34 |
| 7 | 38 |

FIG. 2

$NO_x$ DETECTION APPARATUS AND $NO_x$ SENSOR SYSTEM

CROSS REFERENCE TO RELATED APPLICATIONS

The present application claims priority from Japanese Patent Application No. 2012-251344, which was filed on Nov. 15, 2012, the disclosure of which is herein incorporated by reference in its entirety.

BACKGROUND OF THE INVENTION

1. Field of the Invention

The present invention relates to an $NO_x$ detection apparatus connected to an $NO_x$ sensor which detects the concentration of $NO_x$ contained in a to-be-measured gas, and to an $NO_x$ sensor system.

2. Description of Related Art

A conventionally known $NO_x$ detection apparatus is connected to an $NO_x$ sensor configured by use of a solid electrolyte member, and is used to detect the concentration of $NO_x$ contained in a to-be-measured gas.

In such an $NO_x$ sensor, the to-be-measured gas is introduced into a first measurement chamber through a predetermined diffusion resistor, and the oxygen concentration of the to-be-measured gas is adjusted to a predetermined concentration by means of a first pumping cell which is composed of a solid electrolyte member and a pair of first electrodes. Next, the to-be-measured gas having the adjusted oxygen concentration flows from the first measurement chamber into an $NO_x$ measurement chamber, and $NO_x$ contained in the to-be-measured gas is decomposed by means of a second pumping cell composed of a solid electrolyte member and a pair of second electrodes, whereby a second pumping current corresponding to the $NO_x$ concentration flows between the pair of second electrodes.

The $NO_x$ detection apparatus detects the concentration of $NO_x$ contained in the to-be-measured gas on the basis of the second pumping current output from the $NO_x$ sensor.

Notably, in such an $NO_x$ sensor, which measures the gas concentration ($NO_x$ concentration) on the basis of an output (second pumping current) obtained via a pair of electrodes of the cell, the amount of the gas flowing into measurement chambers (the first measurement chamber and the $NO_x$ measurement chamber) is limited (controlled) by a predetermined diffusion resistor, whereby measurement is stabilized.

However, the conventional $NO_x$ detection apparatus has a problem in that the amount of the gas which flows into the measurement chamber changes in accordance with a change in the pressure of the to-be-measured gas in the vicinity of the attached $NO_x$ sensor, and the sensor output changes with the change in the pressure of the to-be-measured gas even when the gas concentration remains unchanged, and so the measured gas concentration involves an error.

Further, the $NO_x$ sensor has a problem in that the state of variation in the sensor output (output variation state) attributable to a change in the pressure of the to-be-measured gas differs among individual $NO_x$ sensors when the magnitude of the diffusion resistance for introducing the to-be-measured gas into the measurement chamber varies among the individual $NO_x$ sensors due to production variation, etc. of the individual $NO_x$ sensors.

To solve the above-described problem, there has been proposed a technique for suppressing a decrease in gas detection accuracy by means of setting pressure correction information in advance in accordance with the individual difference (individual characteristic) of each sensor and correcting the $NO_x$ concentration by use of the pressure correction information (see Patent Document 1). For example, the $NO_x$ concentration is corrected by use of, as the pressure correction information, Equation 2 which will be described later.

RELATED ART DOCUMENTS

Patent Document 1 is Japanese Patent Application Laid-Open (kokai) No. 2009-210450.

BRIEF SUMMARY OF THE INVENTION

However, in the case where the $NO_x$ concentration is detected on the basis of the second pumping current, the following problem may arise. The second pumping current may not change in proportion to the $NO_x$ concentration if the $NO_x$ concentration falls within a certain concentration range. In such a concentration range, the detected $NO_x$ concentration may involve an error, thereby decreasing the gas detection accuracy.

FIG. 8 shows the relation between $NO_x$ actual concentration and $NO_x$ sensor output for the case where the conventional $NO_x$ detection apparatus is used, wherein a broken line represents a theoretical value and each of six solid lines represents an actual measured value. Notably, this measurements was performed with the gas pressure maintained constant.

As shown in FIG. 8, each of the actual measured values becomes smaller than the theoretical value when the $NO_x$ actual concentration increases. Namely, within a range where the $NO_x$ actual concentration is low, the actual measured value (sensor output) is close to the theoretical value. However, the higher the actual concentration of $NO_x$, the greater the difference between the actual measured value (sensor output) and the theoretical value becomes.

Therefore, even in the case where the gas pressure is constant, if the $NO_x$ concentration is higher than a specific value, the gas detection value calculated from the sensor output may involve an error, which decreases the accuracy in detecting the $NO_x$ concentration.

The present invention has been accomplished in order to solve the above-described problem, and its object is to provide an $NO_x$ detection apparatus which can suppress a decrease in the accuracy in detecting the concentration of $NO_x$ even in the case where a gas detection value calculated from the output of a sensor involves an error within a concentration range where the $NO_x$ concentration is higher than a specific value.

In order to achieve the above-described object, the present invention provides the following means.

An $NO_x$ detection apparatus of the present invention is connected to an $NO_x$ sensor and is adapted to detect an $NO_x$ concentration within a to-be-measured gas. The $NO_x$ sensor includes a first pumping cell which has (includes) paired first electrodes provided (positioned) internally and externally, respectively, of a first measurement chamber and which adjusts the oxygen concentration of the to-be-measured gas introduced into the first measurement chamber (i.e., transforms the to-be-measured gas into an oxygen-concentration-adjusted to-be-measured gas). The $NO_x$ sensor also includes a second pumping cell which has (includes) paired second electrodes provided (positioned) internally and externally, respectively, of an $NO_x$ measurement chamber communicating with the first measurement chamber and which is configured such that a second pumping current flows between the paired second electrodes. The second current corresponds to the $NO_x$ concentration within the to-be-measured gas whose oxygen concentration has been adjusted in the first measurement chamber (i.e., the oxygen-concentration-adjusted to-be-measured gas). The $NO_x$ detection apparatus comprises first concentration computation means for computing a first $NO_x$ concentration on the basis of the second pumping current; specific concentration determination means for determining whether or not the first $NO_x$ concentration is higher than a predetermined specific concentration; and concentration correction means for correcting the first $NO_x$ concentration by using specific concentration correction information set for each $NO_x$ sensor in advance (i.e., predetermined specific concentration correction information). When the specific concentration determination means determines that the first $NO_x$ concentration is higher than the predetermined specific concentration, correction of the first $NO_x$ concentration by the concentration correction means is performed; and when the specific concentration determination means determines that the first $NO_x$ concentration is not higher than the predetermined specific concentration, correction of the first $NO_x$ concentration by the concentration correction means is prohibited (i.e., the concentration correction means does not correct the first $NO_x$ concentration).

That is, this $NO_x$ detection apparatus does not always perform the correction by the concentration correction means, but it determines whether to perform the correction of the first $NO_x$ concentration by the concentration correction means, by determining whether or not the first $NO_x$ concentration, computed on the basis of the second pumping current, is higher than the specific concentration.

Since the first $NO_x$ concentration $NO_{xpo}$ computed on the basis of the second pumping current changes with the actual $NO_x$ concentration, the present $NO_x$ detection apparatus can determine whether to perform the correction of the first $NO_x$ concentration by the concentration correction means, in accordance with the actual $NO_x$ concentration.

Accordingly, the $NO_x$ detection apparatus of the present invention can suppress a decrease in gas detection accuracy even in the case where the gas detection value based on the sensor output involves an error when the $NO_x$ concentration is higher than the specific $NO_x$ concentration.

In the present invention, the concentration correction means may be configured to correct the first $NO_x$ concentration calculated by the first concentration computation means such that the first $NO_x$ concentration has a greater value (i.e., the first concentration computation means increases the first $NO_x$ concentration). Namely, in the case where the first $NO_x$ concentration tends to assume a value smaller than the actual $NO_x$ concentration when the $NO_x$ concentration becomes high, by correcting the first $NO_x$ concentration to a larger value, the error can be reduced whereby a decrease in detection accuracy can be suppressed.

In the present invention, the first concentration computation means may be configured to compute the first $NO_x$ concentration by use of a linear function whose input value is the second pumping current and whose output value is the first $NO_x$ concentration. In this case, the predetermined specific concentration correction information may be a high-order function whose input value is the first $NO_x$ concentration before being corrected and whose output value is the first $NO_x$ concentration after being corrected.

Namely, in the case where the first concentration computation means computes the first $NO_x$ concentration by use of a liner function whose input value is the second pumping current, the amount of increase in the second pumping current corresponding to the amount of increase in the $NO_x$ concentration may decrease when the $NO_x$ concentration increases.

However, the amount of increase in the second pumping current corresponding to the amount of increase in the $NO_x$ concentration can be increased by correcting the first $NO_x$ concentration by using a high-order function as the specific concentration correction information. Thus, the error of the first $NO_x$ concentration caused by a decrease in the increase amount of the second pumping current can be reduced by the correction by the concentration correction means.

Therefore, according to the $NO_x$ detection apparatus of the present invention, even in the case where the amount of increase in the second pumping current corresponding to the amount of increase in the $NO_x$ concentration decreases as the $NO_x$ concentration increases, the error of the first $NO_x$ concentration can be reduced, whereby a decrease in gas detection accuracy can be suppressed.

Notably, a function which includes at least one second-order or higher-order term may be used as a high order function.

In the present invention, the first concentration computation means may be configured to compute a second $NO_x$ concentration on the basis of the second pumping current, and obtain the first $NO_x$ concentration by correcting the second $NO_x$ concentration on the basis of pressure variation correction information which is set for each $NO_x$ sensor in advance (i.e., predetermined pressure variation correction information).

By setting the pressure variation correction information in accordance with the individual difference of each sensor (the characteristic of each sensor), correcting the second $NO_x$ concentration by using the pressure variation correction information, and using the corrected second $NO_x$ concentration as the first $NO_x$ concentration, it is possible to determine whether to perform the correction of the first $NO_x$ concentration by the concentration correction means through use of the first $NO_x$ concentration in which the correction by the pressure variation correction information is reflected. Thus, a decrease in gas concentration accuracy can be suppressed to a greater extent.

The $NO_x$ detection apparatus of the present invention may comprise correction information setting means for setting the predetermined specific concentration correction information on the basis of the second pumping current output at a predetermined $NO_x$ concentration for determination.

Since the second pump current output from the $NO_x$ sensor assumes a value in which the individual difference of the $NO_x$ sensor is reflected, proper specific concentration correction information corresponding to the individual difference of the $NO_x$ sensor can be set by setting the specific concentration correction information on the basis of the second pumping current output at the predetermined $NO_x$ concentration for determination.

The correction information setting means may be configured to set the specific concentration correction information by making use of a map or arithmetic expression which defines the correlation between the specific concentration correction information and the second pumping current output at the $NO_x$ concentration for determination. Specifically, a map or arithmetic expression which defines the correlation between the specific concentration correction information and the second pumping current output at the $NO_x$ concentration for determination is prepared in advance. The correction information setting means sets the specific concentration correction information on the basis of the actually measured value of the second pumping current by making use of the map (or the arithmetic expression).

Alternatively, the correction information setting means may be configured to set the specific concentration correction information by making use of a map or arithmetic expression which defines the correlation between the specific concentration correction information and the detection error at the $NO_x$ concentration for determination. Specifically, a map or arithmetic expression which defines the correlation between the specific concentration correction information and the detection error at the $NO_x$ concentration for determination is prepared in advance. The correction information setting means sets the specific concentration correction information by making use of the map (or the arithmetic expression) and the detection error computed on the basis of the actually measured value of the second pumping current. The detection error may be obtained by computing an $NO_x$ concentration equivalent value on the basis of the actually measured value of the second pumping current, and computing the difference between the $NO_x$ concentration equivalent value and the known gas concentration.

In the case where a map or an arithmetic expression is prepared in advance in the above-described manner, proper specific concentration correction information corresponding to the individual difference of the $NO_x$ sensor can be set by detecting only the second pumping current output at the $NO_x$ concentration for determination, without detecting the second pumping current of the $NO_x$ sensor over a wide range of $NO_x$ concentration.

Notably, when a high-order function is used as the specific concentration correction information, the correction information setting means sets the high-order function on the basis of the actually measured value of the second pumping current output at the $NO_x$ concentration for determination.

In order to achieve the above-described object, the present invention also provides an $NO_x$ sensor system which comprises: an $NO_x$ sensor including a first pumping cell which has (includes) paired first electrodes provided (positioned) internally and externally, respectively, of a first measurement chamber and which adjusts the oxygen concentration of the to-be-measured gas introduced into the first measurement chamber (i.e., transforms the to-be-measured gas into an oxygen-concentration-adjusted to-be-measured gas); and a second pumping cell which has (includes) paired second electrodes provided (positioned) internally and externally, respectively, of an $NO_x$ measurement chamber communicating with the first measurement chamber and which is configured such that a second pumping current flows between the paired second electrodes, the second current corresponding to an $NO_x$ concentration within a to-be-measured gas whose oxygen concentration has been adjusted in the first measurement chamber (i.e., the oxygen-concentration-adjusted to-be-measured gas); and an $NO_x$ detection apparatus according to any one of the above-described embodiments which is connected to the $NO_x$ sensor and is adapted to detect the $NO_x$ concentration within the to-be-measured gas.

Since this $NO_x$ sensor system includes the $NO_x$ detection apparatus according to any one of the above-described embodiments, it provides an action and effects similar to those achieved by the above-described $NO_x$ detection apparatus.

Therefore, according to the $NO_x$ sensor system of the present invention, a decrease in gas detection accuracy can be suppressed even in the case where a gas detection value calculated from the sensor output involves an error within a concentration range where the $NO_x$ concentration is higher than a specific value.

According to the present invention, a decrease in gas detection accuracy can be suppressed even in the case where a gas detection value calculated from the sensor output involves an error within a concentration range where the $NO_x$ concentration is higher than a specific value.

BRIEF DESCRIPTION OF THE DRAWINGS

Illustrative aspects of the invention will be described in detail with reference to the following figures wherein:

FIG. 2 is a table representing a map for determining an $NO_x$ pressure correction coefficient ($k_1$).

DETAIL DESCRIPTION OF EXEMPLARY EMBODIMENTS OF THE INVENTION

Preferred embodiments of the present invention will next be described with reference to the drawings. However, the embodiments to be described below are mere examples of an application of the technical concept of the present invention. The contents of the embodiments should not be construed as limiting the invention.

1. First Embodiment 1-1. Overall Configuration

Figure 1:
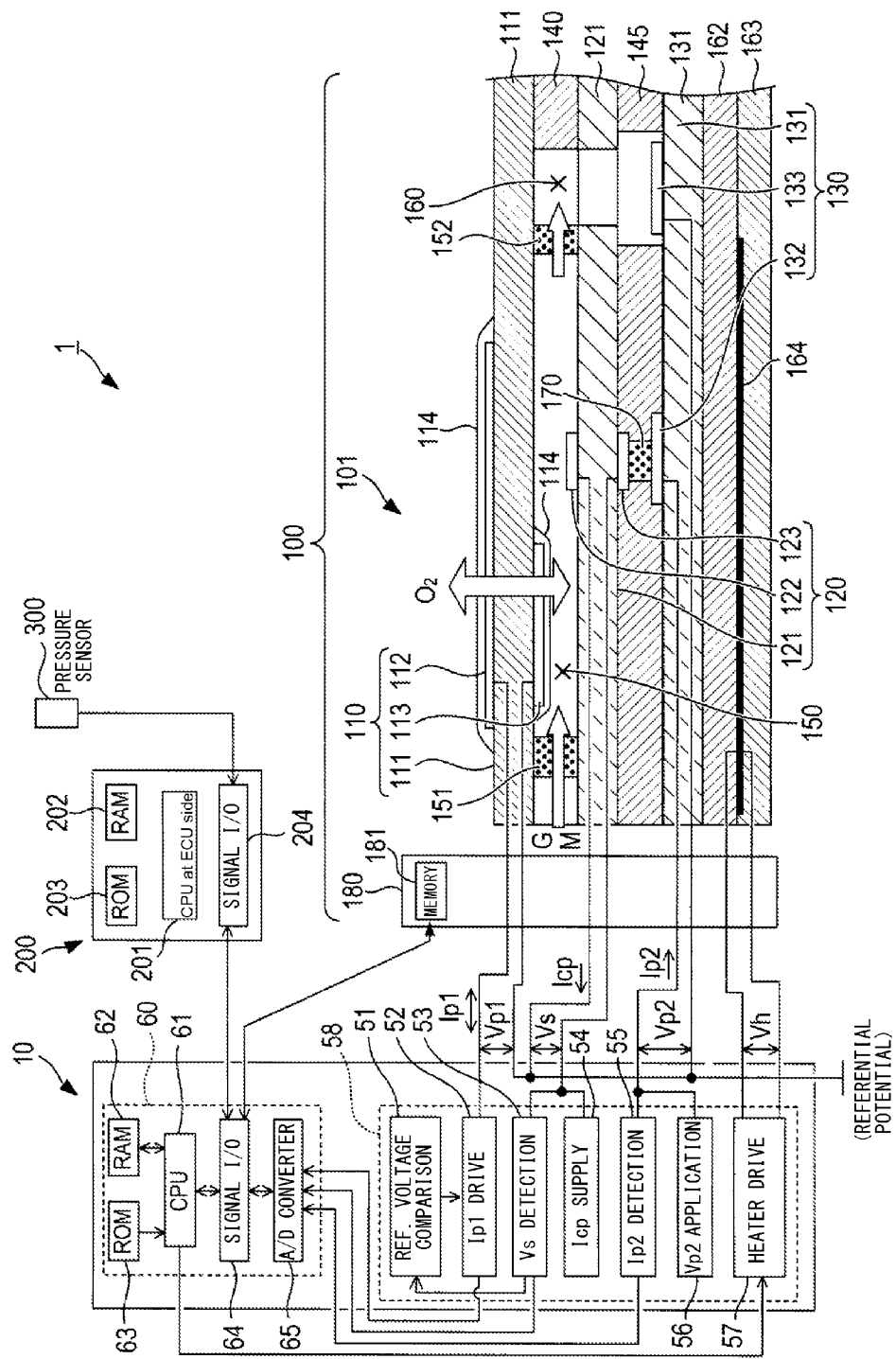
FIG. 1 is a block diagram showing the configuration of an $NO_x$ sensor control apparatus ($NO_x$ detection apparatus) according to a first embodiment of the present invention.

FIG. 1 is a block diagram showing the configuration of an $NO_x$ sensor system 1 according to a first embodiment of the present invention. This embodiment is an example in which the $NO_x$ sensor system 1 corrects an oxygen concentration equivalent value and an $NO_x$ concentration equivalent value in accordance with pressure of exhaust gas.

The $NO_x$ sensor system 1 includes at least an $NO_x$ sensor control apparatus 10 (hereinafter also referred to as an "$NO_x$ detection apparatus 10") and an $NO_x$ sensor 100.

The $NO_x$ detection apparatus 10 is mounted on a vehicle including an unillustrated internal combustion engine (hereinafter also referred to as an "engine"), and is electrically connected to a connector 180 of the $NO_x$ sensor 100. A semiconductor memory 181 (hereinafter also referred to as a "storage means 181"), such as ROM or the like, is incorporated into the connector 180 so as to store various coefficients (to be described later) set for each individual $NO_x$ sensor 100.

Further, the $NO_x$ detection apparatus 10 is electrically connected to a vehicle-side control apparatus 200 (hereinafter may be referred to as an "ECU 200").

The ECU 200 receives data representing oxygen concentration and $NO_x$ concentration within exhaust gas which have been corrected by the $NO_x$ detection apparatus 10, and executes processing for controlling the operation state of the engine, processing for removing $NO_x$ accumulated in catalyst, and other processing on the basis of the received data. Further, the ECU 200 acquires from a pressure sensor 300 information representing the pressure of exhaust gas flowing through an exhaust pipe, and sends the information to the $NO_x$ detection apparatus 10.

Notably, the method of acquiring the information representing the pressure of the exhaust gas is not limited to acquiring it from the pressure sensor 300. For example, the ECU 200 reads the rotational speed and load of the engine, and determines the pressure of the exhaust gas from these pieces of information and by use of a map or calculation equation previously stored in ROM 203.

The ECU 200 includes an ECU-side CPU (central processing unit) 201, RAM 202, ROM 203, a signal input/output section 204, and an unillustrated clock generator. Programs stored in the ROM or the like in advance are executed by the CPU.

The $NO_x$ detection apparatus 10 includes a control circuit 58 and a microcomputer 60 provided on a circuit board. The microcomputer 60, which controls the entirety of the $NO_x$ detection apparatus 10, includes a CPU (central processing unit) 61, RAM 62, ROM 63, a signal input/output section 64, an A/D converter 65, and an unillustrated clock generator. Programs stored in the ROM 63 or the like in advance are executed by the CPU.

The control circuit 58 includes a reference-voltage comparison circuit 51, an Ip1 drive circuit 52, a Vs detection circuit 53, an Icp supply circuit 54, an Ip2 detection circuit 55, a Vp2 application circuit 56, and a heater drive circuit 57. The control circuit 58 controls the $NO_x$ sensor 100, detects first and second pumping currents flowing through the $NO_x$ sensor 100, and outputs the detected first and second pumping currents to the microcomputer 60.

Next, the configuration of the $NO_x$ sensor 100 will be described. The $NO_x$ sensor 100 includes an $NO_x$ sensor element 101; a housing which accommodates the $NO_x$ sensor element 101; a connector 180 for connecting the $NO_x$ sensor element 101 and the $NO_x$ detection apparatus 10; and a lead wire connected to the $NO_x$ sensor element 101. Since the structure of the sensor itself is known, only the $NO_x$ sensor element 101 of the $NO_x$ sensor 100 will be described below with reference to a longitudinal cross sectional view of the $NO_x$ sensor element 101.

The $NO_x$ sensor element 101 has a layered structure formed by stacking a first solid electrolyte layer 111, an insulation layer 140, a second solid electrolyte layer 121, an insulation layer 145, a third solid electrolyte layer 131, and insulation layers 162 and 163 in this sequence. A first measurement chamber 150 is defined between the first solid electrolyte layer 111 and the second solid electrolyte layer 121. A to-be-measured gas GM is introduced from the outside into the first measurement chamber 150 via a first diffusion resistor 151 disposed at the inlet (the left end in FIG. 1) of the first measurement chamber 150.

A second diffusion resistor 152 is disposed at the end of the first measurement chamber 150 opposite the inlet thereof. A second measurement chamber 160 (corresponding to the "$NO_x$ measurement chamber" of the present invention) is defined on the right side of the first measurement chamber 150, and communicates therewith via the second diffusion resistor 152. The second measurement chamber 160 is formed between the first solid electrolyte layer 111 and the third solid electrolyte layer 131 such that the second measurement chamber 160 penetrates through the second solid electrolyte layer 121.

An elongated plate-shaped heater 164, which extends along the longitudinal direction of the $NO_x$ sensor element 101, is embedded between the insulation layers 162 and 163. The heater 164 is used to heat the gas sensor to an activation temperature so as to increase the oxygen-ion conductivity of the solid electrolyte layer, to thereby stabilize the operation of the gas sensor.

The insulation layers 140 and 145 are formed mainly of alumina, and the first and second diffusion resistors 151 and 152 are formed of a porous material such as alumina. Further, the heater 164 is formed of platinum or the like.

A first pumping cell 110 includes the first solid electrolyte layer 111, which is formed mainly of zirconia having oxygen-ion conductivity; and paired inside and outside first pumping electrodes 113 and 112 disposed to sandwich the first solid electrolyte layer 111. The inside first pumping electrode 113 faces the first measurement chamber 150. Each of the inside and outside first pumping electrodes 113 and 112 is formed mainly of platinum; and the surface of each electrode is covered by a protection layer 114 formed of a porous material.

An oxygen concentration detection cell 120 includes the second solid electrolyte layer 121, which is formed mainly of zirconia; and a detection electrode 122 and a reference electrode 123 disposed to sandwich the second solid electrolyte layer 121. The detection electrode 122 faces the first measurement chamber 150 at a location downstream of the inside first pumping electrode 113. Each of the detection electrodes 122 and 123 is formed mainly of platinum.

Notably, the insulation layer 145 is cut out to form a cut-out such that the reference electrode 123 in contact with the second solid electrolyte layer 121 is disposed in the cut-out; and the cut-out is filled with a porous material, whereby a reference oxygen chamber 170 is formed. A constant weak current is supplied in advance to the oxygen concentration detection cell 120 by use of the Icp supply circuit 54, whereby oxygen is fed from the first measurement chamber 150 into the reference oxygen chamber 170 so as to establish an oxygen reference.

A second pumping cell 130 includes the third solid electrolyte layer 131, which is formed mainly of zirconia; an inside second pumping electrode 133 disposed on a surface region of the third solid electrolyte layer 131, whose surface region faces the second measurement chamber 160; and a counterpart second pumping electrode 132, which forms a pair together with the inside second pumping electrode 133. Each of the inside second pumping electrode 133 and the counterpart second pumping electrode 132 is formed mainly of platinum.

Notably, the counterpart second pumping electrode 132 is disposed on the third solid electrolyte layer 131 at a location corresponding to the cut-out of the insulation layer 145, so that the counterpart second pumping electrode 132 faces the reference electrode 123 via the reference oxygen chamber 170.

The inside first pumping electrode 113, the detection electrode 122, and the inside second pumping electrode 133 are connected to a reference potential. The outside first pumping electrode 112 is connected to the Ip1 drive circuit 52, and the reference electrode 123 is connected to the Vs detection circuit 53 and the Icp supply circuit 54 in parallel. Further, the counterpart second pumping electrode 132 is connected to the Ip2 detection circuit 55 and the Vp2 application circuit 56 in parallel. The heater drive circuit 57 is connected to the heater 164.

The various circuits included in the control circuit 58 have the following functions.

The Ip1 drive circuit 52 supplies a first pumping current Ip1 between the inside first pumping electrode 113 and the outside first pumping electrode 112, while detecting the first pumping current Ip1. At that time, a voltage Vp1 is generated between the inside first pumping electrode 113 and the outside first pumping electrode 112.

The Vs detection circuit 53 detects an inter-electrode voltage Vs between the detection electrode 122 and the reference electrode 123, and outputs the detection result to the reference-voltage comparison circuit 51.

The reference-voltage comparison circuit 51 compares a reference voltage (e.g., 425 mV) and the output of the Vs detection circuit 53, and outputs a comparison result to the Ip1 drive circuit 52. The Ip1 drive circuit 52 controls the Ip1 current such that the inter-electrode voltage Vs becomes equal to the above-described reference voltage, to thereby adjust the oxygen concentration within the first measurement chamber 150 to a level at which $NO_x$ does not decompose.

The Icp supply circuit 54 causes a weak current Icp to flow between the detection electrode 122 and the reference electrode 123 so as to feed oxygen from the first measurement chamber 150 into the reference oxygen chamber 170, to thereby expose the reference electrode 123 to a predetermined oxygen concentration, which serves as a reference.

The Vp2 application circuit 56 applies a constant voltage Vp2 (e.g., 450 mV) between the inside second pumping electrode 133 and the counterpart second pumping electrode 132, the voltage being determined such that the $NO_x$ gas within the to-be-measured gas GM is decomposed into oxygen ($O_2$) and nitrogen ($N_2$). Thus, the $NO_x$ is decomposed into nitrogen and oxygen.

The Ip2 detection circuit 55 detects a second pumping current Ip2 which flows through the second pumping cell 130 so as to pump out from the second measurement chamber 160 the oxygen produced as a result of decomposition of $NO_x$.

The Ip1 drive circuit 52 outputs the detected value of the first pumping current Ip1 to the A/D converter 65. Further, the Ip2 detection circuit 55 outputs the detected value of the second pumping current Ip2 to the A/D converter 65.

The A/D converter 65 converts these values to digital values, and outputs them to the CPU 61 via the signal input/output section 64.

Next, an example of control of the $NO_x$ sensor 100 performed by use of the control circuit 58 will be described. First, when electrical power is supplied from an external power supply upon startup of the engine, the heater 164 is activated by a heater voltage Vh applied thereto via the heater drive circuit 57 so as to heat the first pumping cell 110, the oxygen concentration detection cell 120, and the second pumping cell 130 to the activation temperature. Further, the Icp supply circuit 54 causes the weak current Icp to flow between the detection electrode 122 and the reference electrode 123. Thus, oxygen is fed from the first measurement chamber 150 into the reference oxygen chamber 170 to be used as a reference.

After completion of heating of the cells 110, 120, and 130 to the activation temperature, the first pumping cell 110 pumps out oxygen contained in the to-be-measured gas (exhaust gas) GM having flowed into the first measurement chamber 150 such that the oxygen flows from the inside first pumping electrode 113 toward the outside first pumping electrode 112.

At that time, the oxygen concentration within the first measurement chamber 150 corresponds to the inter-electrode voltage (inter-terminal voltage) Vs of the oxygen concentration detection cell 120. Therefore, the Ip1 drive circuit 52 controls the first pumping current Ip1, which flows through the first pumping cell 110, such that the inter-electrode voltage Vs becomes equal to the above-described reference voltage, to thereby adjust the oxygen concentration within the first measurement chamber 150 to a level at which $NO_x$ decomposes as little as possible.

The to-be-measured gas GM having the adjusted oxygen concentration further flows toward the second measurement chamber 160. The Vp2 application circuit 56 applies, as the inter-electrode voltage (inter-terminal voltage) of the second pumping cell 130, the constant voltage Vp2 determined such that the $NO_x$ gas within the to-be-measured gas GM is decomposed into oxygen and $N_2$ gas (a voltage (e.g., 450 mV) higher than the control voltage of the oxygen concentration detection cell 120), to thereby decompose the $NO_x$ into nitrogen and oxygen. Thus, the second pumping current Ip2 flows through the second pumping cell 130 such that the oxygen produced as a result of the decomposition of the $NO_x$ is pumped out from the second measurement chamber 160. Since a linear relation exists between the second pumping current Ip2 and the $NO_x$ concentration, the $NO_x$ concentration within the to-be-measured gas can be detected from the second pumping current Ip2 detected by the Ip2 detection circuit 55.

1.2 Pressure Correction for $NO_x$ Concentration

In the $NO_x$ detection apparatus 10 according to the first embodiment of the present invention, the pressure correction for the $NO_x$ concentration is performed in accordance with the following Equation 1.

$$Rno = NO_{xpo} \cdot \left[ 1 + \frac{\Delta NO}{100} \right] \quad (1)$$

Notably, Rno represents corrected $NO_x$ concentration, $NO_{xpo}$ represents a value obtained by Equation 2, and $\Delta NO$ represents a value obtained by Equation 3.

$$NO_{xpo} = NO_{xp} \cdot \left[ \frac{k_1 + P}{P} \right] \cdot \left[ \frac{Po}{k_1 + Po} \right] \quad (2)$$

$$\Delta NO = (a \cdot \Delta P^2 + b \cdot \Delta P) x C \quad (3)$$

Notably, in Equation 2, $NO_{xp}$ represents $NO_x$ concentration at pressure P before pressure correction (second $NO_x$ concentration calculated from the second pumping current); $NO_{xpo}$ represents $NO_x$ concentration at pressure Po after pressure correction (first $NO_x$ concentration); P represents the pressure (kPa) of the to-be-measured gas; Po represents the atmospheric pressure (=101.3 kPa); and $k_1$ represents an $NO_x$ pressure correction coefficient ($NO_x$ pressure correction information). Correction coefficients a and b in Equation 3 are determined through the processing performed in step S16 or S20 of a concentration detection processing routine which will be described later. Notably, in Equation 3, $\Delta P$ represents a value obtained by subtracting the atmospheric pressure Po from the pressure P of the to-be-measured gas, and a constant C represents individual information which is set in advance for each $NO_x$ sensor 100 and which is stored in the semiconductor memory 181.

Notably, since the second pumping current Ip2 has a fixed relation with the $NO_x$ concentration within the to-be-measured gas, the second $NO_x$ concentration $NO_{xp}$ at the pressure P can be calculated from the second pumping current Ip2. The microcomputer 60 performs this calculation by reading out of the ROM 63 an equation representing the relation between Ip2 and the $NO_x$ concentration within the to-be-measured gas.

The $NO_x$ pressure correction coefficient ($k_1$) is selected from a map shown in FIG. 2. A value of $k_1$ corresponding to a rank assigned to an individual $NO_x$ sensor is set as the $NO_x$ pressure correction coefficient for the $NO_x$ sensor. Notably, each $NO_x$ detection apparatus uses only one of the above-described correction ranks. In this case, before the $NO_x$ detection apparatus is shipped out, the map of FIG. 2 is previously stored in the semiconductor memory 181 of the individual $NO_x$ sensor.

Each $NO_x$ sensor is connected to an external testing device, and an $NO_x$ concentration equivalent value is calculated from the second pumping current Ip2 in a state in which a reference gas is used and the gas pressure is selectively set to a plurality of known gas pressures, whereby the value of $k_1$ is determined. For example, in the case where the $NO_x$ concentration was measured at two points, the value of $k_1$ is determined from the slope of a straight line connecting the two points. Subsequently, a rank shown in the map of FIG. 2 whose value of $k_1$ is closest to the above-mentioned value of $k_1$ determined from the slope is selected, and is used for the $NO_x$ sensor. For example, a flag indicating the rank is set in the map. Thus, only data corresponding to a single correction rank within the map is referred to. Notably, a gas containing NO (90 ppm), $H_2O$ (3%), $O_2$ (9%), and $N_2$ (balance) was used as the reference gas. In this manner, the value of $k_1$ for each individual $NO_x$ sensor is stored in the semiconductor memory 181.

Notably, in the case where the $NO_x$ concentration was measured at three or more points, the value of $k_1$ may be set as a predetermined curve or a map in which a coefficient is assigned to each of pressure ranges.

The method for pressure correction is not limited to use of functions such as Equations 1 to 3, and a map in which a correction amount is assigned to each of pressure ranges may be used.

In the $NO_x$ detection apparatus 10 according to the first embodiment of the present invention, the pressure correction for the oxygen concentration is performed in accordance with the following Equation 4, wherein $O_P$ represents an oxygen concentration at pressure P before pressure correction (oxygen concentration equivalent value calculated from the first pumping current); $O_{Po}$ represents oxygen concentration at pressure Po after pressure correction (oxygen concentration equivalent value); P represents the pressure (kPa) of the to-be-measured gas; Po represents the atmospheric pressure (=101.3 kPa); and $k_2$ represents an oxygen pressure correction coefficient (oxygen pressure correction information).

$$O_{po} = O_p \cdot \left[\frac{k_2 + P}{P}\right] \cdot \left[\frac{Po}{k_2 + Po}\right] \quad (4)$$

Notably, since the first pumping current Ip1 has a fixed relation with the oxygen concentration within the to-be-measured gas, the uncorrected oxygen concentration $O_P$ at the pressure P can be calculated from the first pumping current Ip1. Specifically, the microcomputer 60 performs this calculation by reading out of the ROM 63 an equation representing the relation between the first pumping current Ip1 and the oxygen concentration within the to-be-measured gas.

The oxygen pressure correction coefficient ($k_2$) is selected from a map similar to that shown in FIG. 2. A value of $k_2$ corresponding to a rank assigned to the individual $NO_x$ sensor is set as the oxygen pressure correction coefficient for the $NO_x$ sensor. Thus, a selected value of $k_2$ is stored in the semiconductor memory 181. Similar to the above-described $k_1$, the value of $k_2$ is determined by connecting each $NO_x$ sensor to an external testing device, and calculating an oxygen concentration equivalent value from the first pumping current Ip1 in a state in which a reference gas is used and the gas pressure is selectively set to a plurality of known gas pressures.

1-3. Correction of $NO_x$ Concentration in the Case Where it is Higher than a Specific Concentration In the $NO_x$ detection apparatus 10 according to the first embodiment of the present invention, the first $NO_x$ concentration $NO_{xpo}$ is corrected in accordance with the following Equation 5 in the case where the first $NO_x$ concentration $NO_{xpo}$, which is calculated from the second pumping current Ip2, is higher than a specific concentration.

$$Y = \alpha \cdot x^2 + \beta \cdot x + \gamma \quad (5)$$

Notably, in Equation 5, a variable X represents a "first $NO_x$ concentration before correction" (first $NO_x$ concentration $NO_{xpo}$), and a variable Y represents a "first $NO_x$ concentration after correction". Further, coefficients $\alpha$, $\beta$, and $\gamma$ are set in advance for each individual $NO_x$ sensor 100. Before the $NO_x$ detection apparatus is shipped out, values of the coefficients $\alpha$, $\beta$, and $\gamma$ are stored in the semiconductor memory 181 of each $NO_x$ sensor.

Specifically, each $NO_x$ sensor is connected to an external testing device, and an $NO_x$ concentration equivalent value is calculated from the second pumping current IP2 in a state in which a gas for determination is used and the gas concentration is set to a known gas concentration, whereby a difference (output drop ratio [%]) between the value of the known gas concentration and the $NO_x$ concentration equivalent value is detected. Subsequently, values of the coefficients $\alpha$, $\beta$, and $\gamma$ are determined on the basis of the output drop ratio and the map data shown in FIG. 5.

Figure 5:
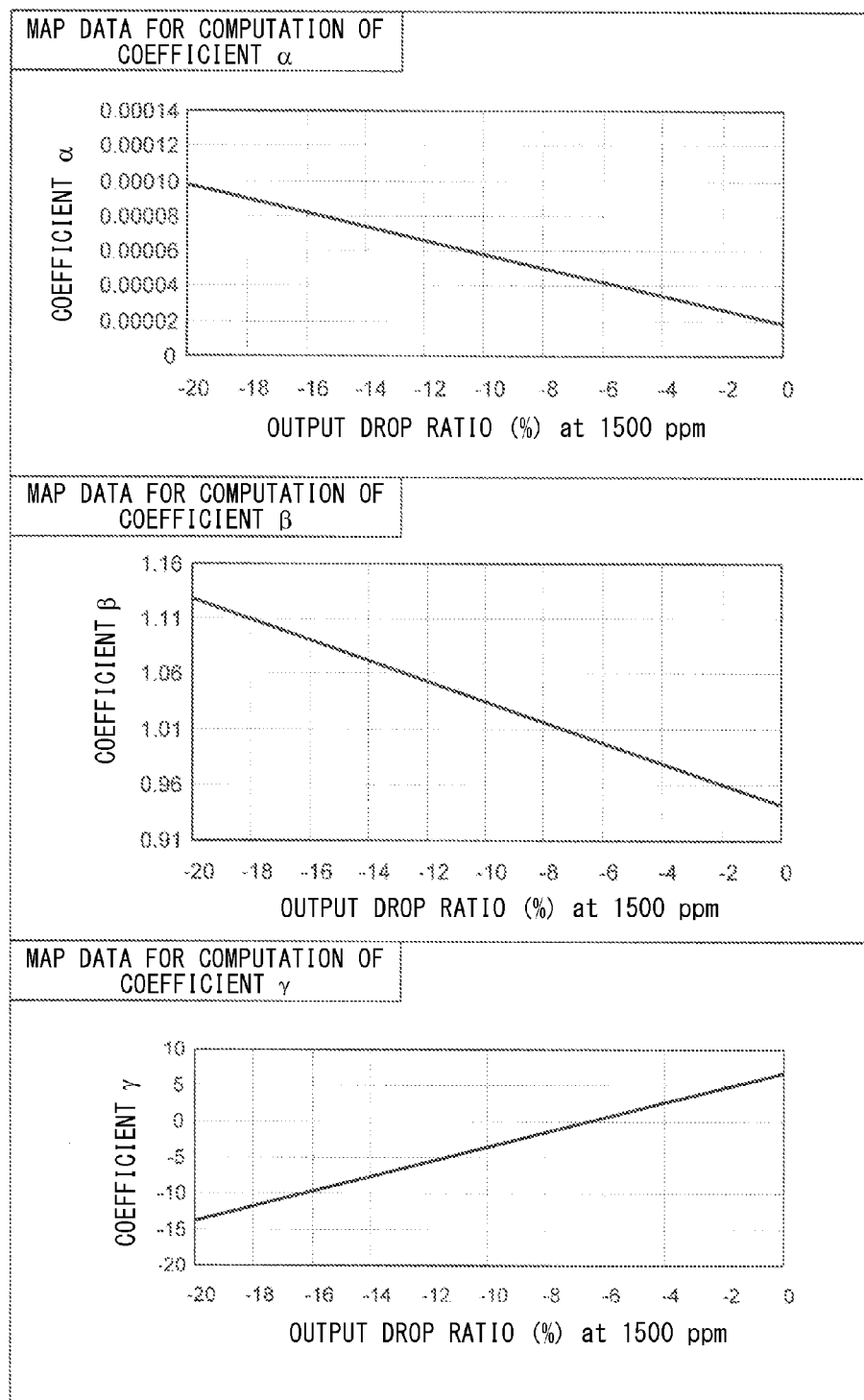
FIG. 5 includes graphs showing example map data sets used for computing correction coefficients $\alpha$, $\beta$, and $\gamma$, respectively.

Notably, the map data shown in FIG. 5 is stored in the external testing device, and the values of the coefficients $\alpha$, $\beta$, and $\gamma$ for each $NO_x$ sensor are stored in the semiconductor memory 181 in accordance with the results of detection of the output drop ratio. FIG. 5 shows an example of map data for determining the values of the coefficients $\alpha$, $\beta$, and $\gamma$ on the basis of the output drop ratio detected when a gas whose $NO_x$ concentration is 1500 ppm is used as a gas for determination.

Correction of the first $NO_x$ concentration $NO_{xpo}$ by use of Equation 5 is carried out as the processing performed in step S18 of the concentration detection processing routine which will be described later.

1-4. Concentration Detection Processing

Figure 3A:
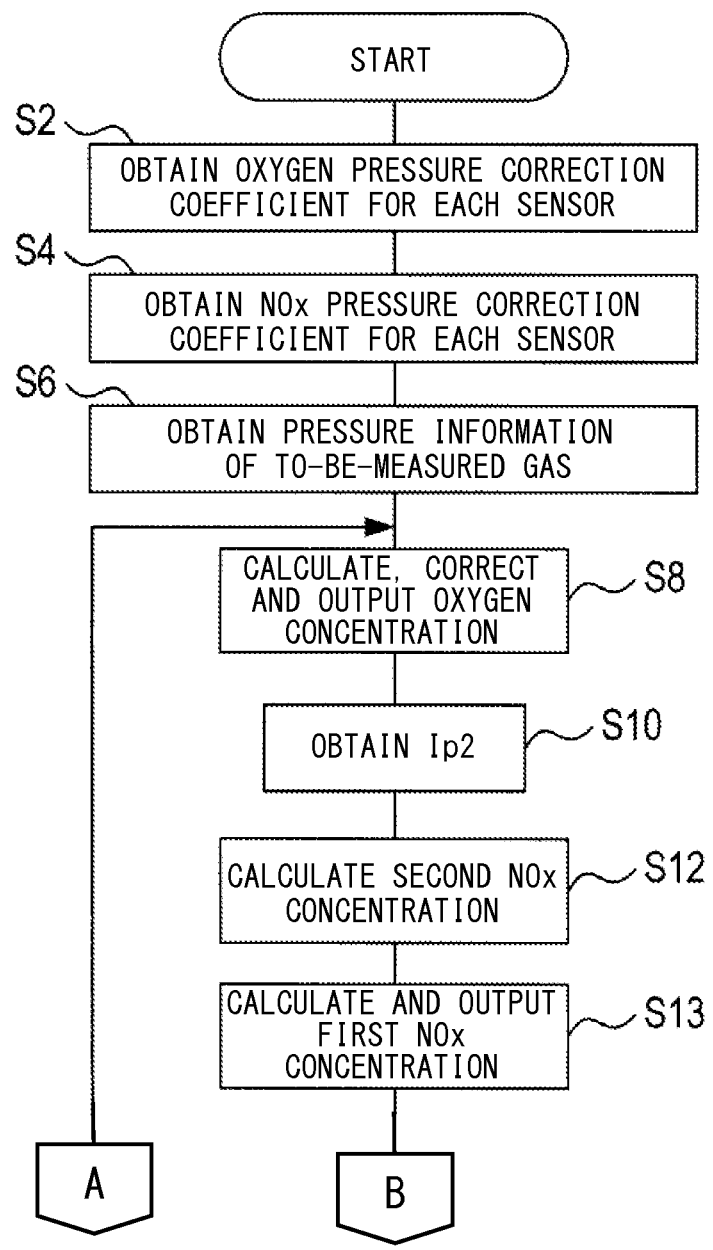
FIGS. 3A and 3B are flowcharts showing the details of concentration detection processing performed in the $NO_x$ detection apparatus.
Figure 3B:
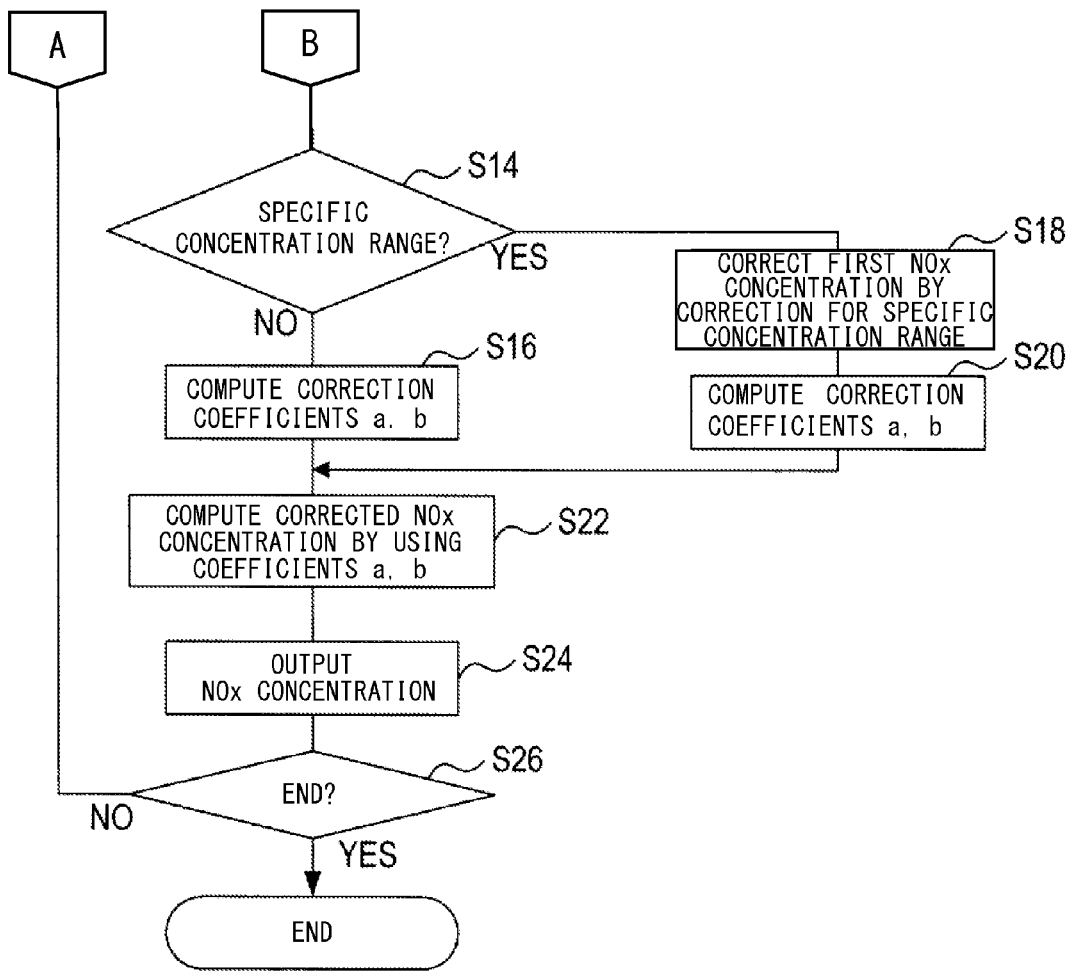

Next, concentration detection processing performed by the $NO_x$ detection apparatus 10 according to the first embodiment of the present invention will be described in detail with reference to flowcharts of FIGS. 3A and 3B. Notably, the concentration detection processing is performed by the microcomputer 60.

Upon start of the concentration detection processing, in step S2, the microcomputer 60 accesses the semiconductor memory 181 mounted on the connector 180 of the $NO_x$ sensor 100, and acquires the oxygen pressure correction coefficient ($k_2$) from the semiconductor memory 181.

In step S4, the microcomputer 60 accesses the semiconductor memory 181, and acquires the $NO_x$ pressure correction coefficient ($k_1$) from the semiconductor memory 181.

In step S6 subsequent thereto, the microcomputer 60 acquires the pressure of the to-be-measured gas (pressure information) via the ECU 200.

Next, in step S8, the microcomputer 60 calculates an oxygen concentration, corrects the calculated oxygen concentration, and outputs the corrected oxygen concentration.

Specifically, in step S8, the microcomputer 60 first acquires a value of the first pumping current Ip1 from the Ip1 drive circuit 52 (in actuality, a detection signal generated through voltage conversion of the first pumping current Ip1). The microcomputer 60 then reads out of the ROM 63 an equation representing the relation between the first pumping current Ip1 and the oxygen concentration of the to-be-measured gas, and calculates the oxygen concentration $O_P$ (the oxygen concentration equivalent value $O_P$) before pressure correction. Next, the microcomputer 60 applies the oxygen pressure correction coefficient and the pressure of the to-be-measured gas obtained in steps S2 and S6 to Equation 4 so as to calculate the corrected oxygen concentration $O_{Po}$. Here, $O_{Po}$ represents the oxygen concentration at the pressure Po (atmospheric pressure). The microcomputer 60 then outputs (transmits) the calculated oxygen concentration $O_{Po}$ to the ECU 200 via the signal input/output section 64.

In the subsequent step S10, the microcomputer 60 acquires a value of the second pumping current Ip2 from the Ip2 detection circuit 55 (in actuality, a detection signal generated through voltage conversion of the second pumping current Ip2).

Next, in step S12, the microcomputer 60 reads out of the ROM 63 an equation representing the relation between the second pumping current Ip2 and the $NO_x$ concentration of the to-be-measured gas, and calculates the second $NO_x$ concentration (the $NO_x$ concentration at pressure P before pressure correction) $NO_{xP}$.

Notably, in the present embodiment, a liner function (y=Ax+B) whose input value is the second pumping current Ip2 and whose output value is the second $NO_x$ concentration $NO_{xp}$ is set as the relation equation used in step S12. Notably, x represents the second pumping current Ip2, y represents the second $NO_x$ concentration $NO(NO_x$ concentration equivalent value), A represents a coefficient, and B represents a constant term. Values appropriate for each $NO_x$ sensor 100 are set as the coefficients A and the constant term B.

Next, in step S13, the microcomputer 60 calculates the first $NO_x$ concentration ($NO_x$ concentration at pressure Po after pressure correction) $NO_{xpo}$, and outputs the calculation result.

Specifically, in step S13, the microcomputer 60 applies to the above-described Equation 2 the second $NO_x$ concentration $NO_{xp}$ and the $NO_x$ pressure correction coefficient and the pressure of the to-be-measured gas which have been acquired in steps S4 and S6, to thereby calculate the first $NO_x$ concentration ($NO_x$ concentration after pressure correction) $NO_{xpo}$. Here, the first $NO_x$ concentration $NO_{xpo}$ is a value at the pressure Po (atmospheric pressure). The microcomputer 60 then outputs (transmits) the calculated first $NO_x$ concentration $NO_{xpo}$ to the ECU 200 via the signal input/output section 64.

Next, in step S14, the microcomputer 60 determines whether or not the first $NO_x$ concentration $NO_{xpo}$ falls in a predetermined specific concentration range. In the case where the microcomputer 60 makes an "Yes" determination, it proceeds to step S18. In the case where the microcomputer 60 makes a "No" determination, it proceeds to step S16. In the $NO_x$ detection apparatus 10 of the present embodiment, a "concentration range of 90 ppm or higher" is set as the specific concentration range.

Upon making a "No" determination in step S14, in step S16, the microcomputer 60 reads out of the semiconductor memory 181 the map data which has been prepared in advance, and calculates the correction coefficients a and b from the first $NO_x$ concentration $NO_{xpo}$ by use of the map data. The correction coefficients a and b are the coefficients in the above-described Equation 3. Equation 3 is used for correction processing performed in step S22 which will be described later.

Figure 4:
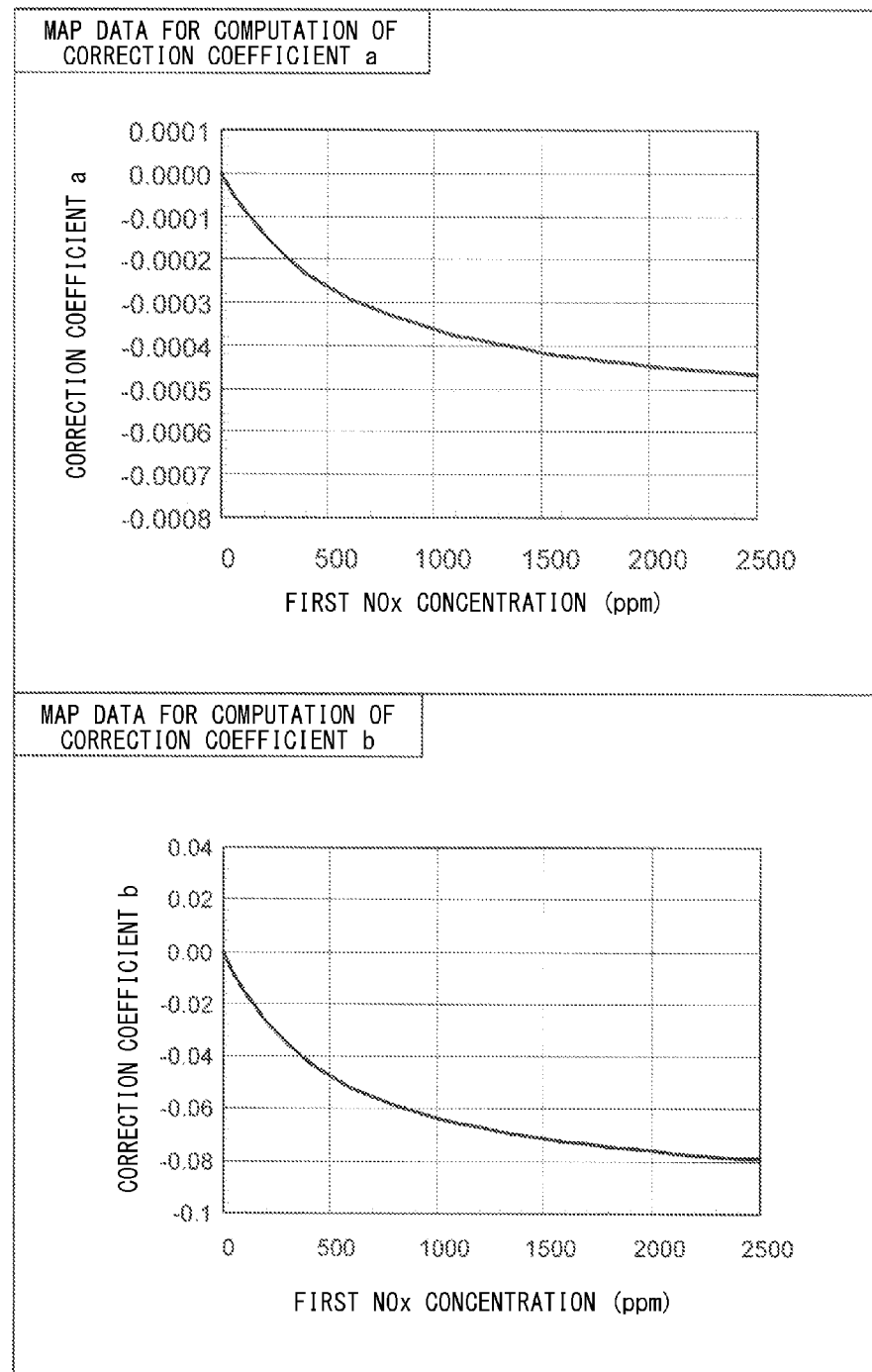
FIG. 4 includes graphs showing example map data sets used for computing correction coefficients a and b, respectively.

FIG. 4 shows an example of the map data used in the above-described computation processing. The map data concerning the correction coefficients a and b is set in advance for each $NO_x$ sensor 100. Before the $NO_x$ detection apparatus is shipped out, the map data is stored in the semiconductor memory 181 of each $NO_x$ sensor.

Upon making an "Yes" determination in step S14, in step S18, the microcomputer 60 corrects the first $NO_x$ concentration $NO_{xpo}$ by use of an equation which is adapted for correction for the specific concentration range (hereinafter referred to as the "correction equation for specific concentration range") and which is set in advance for each $NO_x$ sensor 100. Specifically, the microcomputer 60 corrects the first $NO_x$ concentration $NO_{xpo}$ by use of the correction equation for specific concentration range; namely, the above-described Equation 5.

As described above, the coefficients α, β, and γ are set in advance for each $NO_x$ sensor 100. Before the $NO_x$ detection apparatus is shipped out, the values of the coefficients α, β, and γ are stored in the semiconductor memory 181 of each individual $NO_x$ sensor. Further, as mentioned above, the $NO_x$ concentration equivalent value is calculated from the second pumping current Ip2 in a state in which a gas for determination is used and the gas concentration is set to a known gas concentration. Then, the difference (output drop ratio [%]) between the known gas concentration and the $NO_x$ concentration equivalent value is detected, and the values of the coefficients α, β, and γ are determined on the basis of the output drop ratio and the map data shown in FIG. 5.

Next, in step S20, the microcomputer 60 determines the correction coefficients a and b on the basis of the first $NO_x$ concentration $NO_{xpo}$ corrected in step S18, while referring to the map data prepared in advance.

Notably, the map data used in step S20 is the same as that used in step S16.

After completion of step S16 or S20, in step S22, the microcomputer 60 corrects the first $NO_x$ concentration $NO_{xpo}$ by use of a pressure variation correction equation which is set for each $NO_x$ sensor 100 in advance. Specifically, the above-described Equation 1 is the pressure variation correction equation. The microcomputer 60 calculates the corrected $NO_x$ concentration Rno by use of Equation 1 with Equation 3 substituted into ΔNO of Equation 1.

In step S24 subsequent thereto, the microcomputer 60 outputs (transmits), as the "$NO_x$ concentration," the corrected $NO_x$ concentration Rno calculated in step S22 to the ECU 200 via the signal input/output section 64.

In step S26 subsequent thereto, the microcomputer 60 determines whether to end the concentration detection processing. In the case where the microcomputer 60 makes an "Yes" determination, it ends this processing. In the case where the microcomputer makes a "No" determination, it returns to step S8, and repeatedly executes steps S8 to S26 until it makes an "Yes" determination in step S26.

By means of executing the concentration detection processing as described above, the microcomputer 60 can correct the $NO_x$ concentration detected from the second pumping current Ip2 of the $NO_x$ sensor 100.

1-5. Comparative Measurements

In order to verify the effect of the correction performed by the $NO_x$ detection apparatus 10 of the present embodiment, measurements were performed by use of the $NO_x$ detection apparatus 10 and a conventional $NO_x$ detection apparatus, and the results of measurements were compared. The results of the measurements will be described below.

In a first comparative measurement, the concentration of $NO_x$ was measured in a state in which correction was performed by the method of the present embodiment and in a state in which correction was performed by the conventional method. In this first comparative measurement, the $NO_x$ concentration was set to 1500 ppm, and the pressure of the to-be-measured gas was changed.

Notably, the $NO_x$ concentration corrected by the conventional method refers to the $NO_x$ concentration corrected by use of only the above-described Equation 2. Namely, the $NO_x$ concentration corrected by the conventional method refers to the $NO_x$ concentration corrected without reflecting the effect of Equation 3 which is substituted into the above-described Equation 1.

Figure 6:
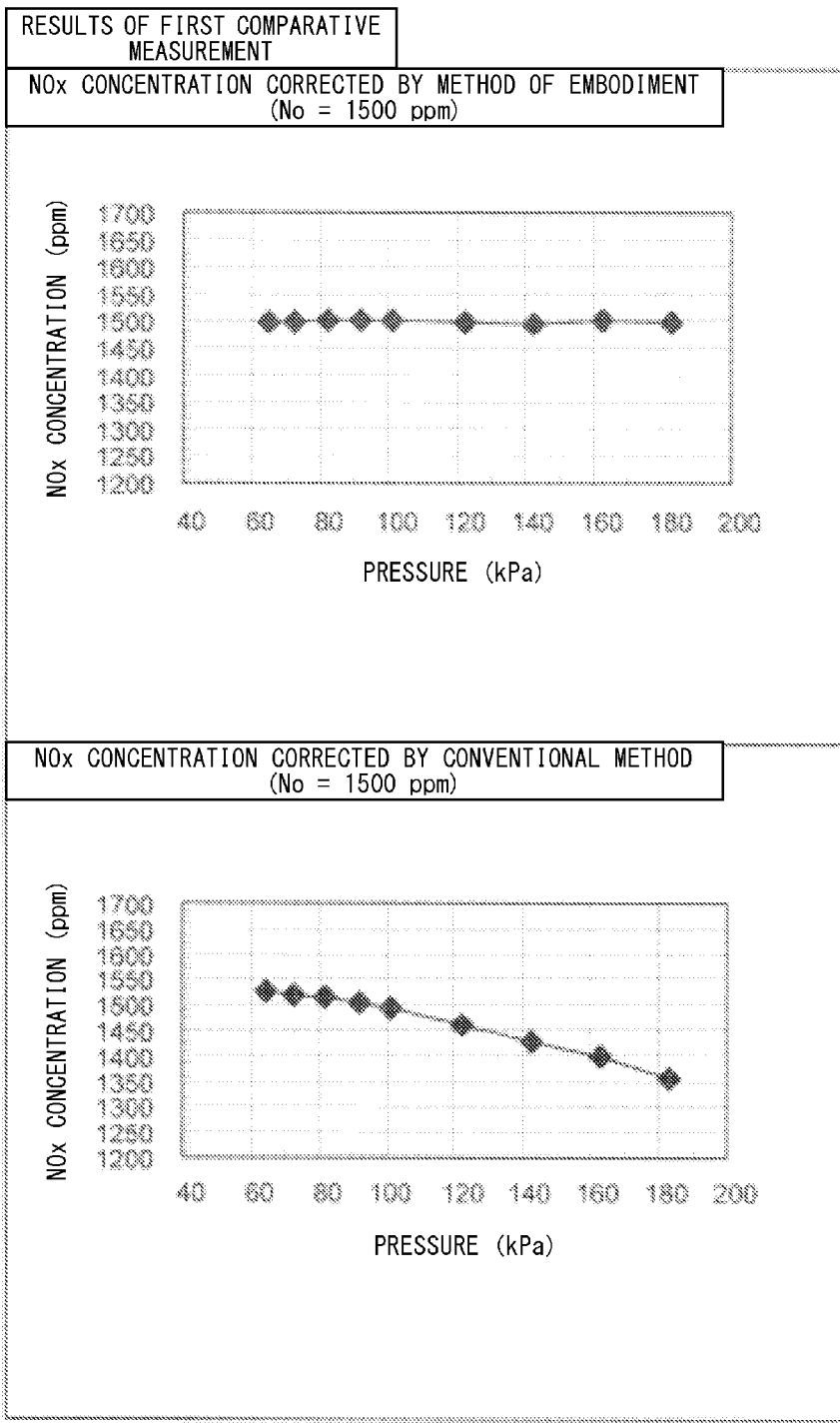
FIG. 6 includes graphs showing the results of a first comparative measurement.

FIG. 6 shows the result of the first comparative measurement.

As shown in FIG. 6, the $NO_x$ concentration corrected by the method of the present embodiment is nearly equal to the actual $NO_x$ concentration (1500 ppm) irrespective of a change in the pressure of the to-be-measured gas. This demonstrates that the $NO_x$ concentration can be detected with reduced influences of a change in the pressure of the to-be-measured gas.

Meanwhile, since the $NO_x$ concentration corrected by the conventional method differs little from the actual $NO_x$ concentration (1500 ppm) within a range where the pressure of the to-be-measured gas is between 60 and 120 kPa, the effect of correction is observed. However, within a range where the pressure of the to-be-measured gas exceeds 120 kPa, the difference from the actual $NO_x$ concentration increases with increasing pressure.

As seen from the above, the $NO_x$ detection apparatus 10 of the present invention can accurately detect gas even in the case where the pressure of the to-be-measured gas varies in a state in which the $NO_x$ concentration is 1500 ppm.

Figure 9:
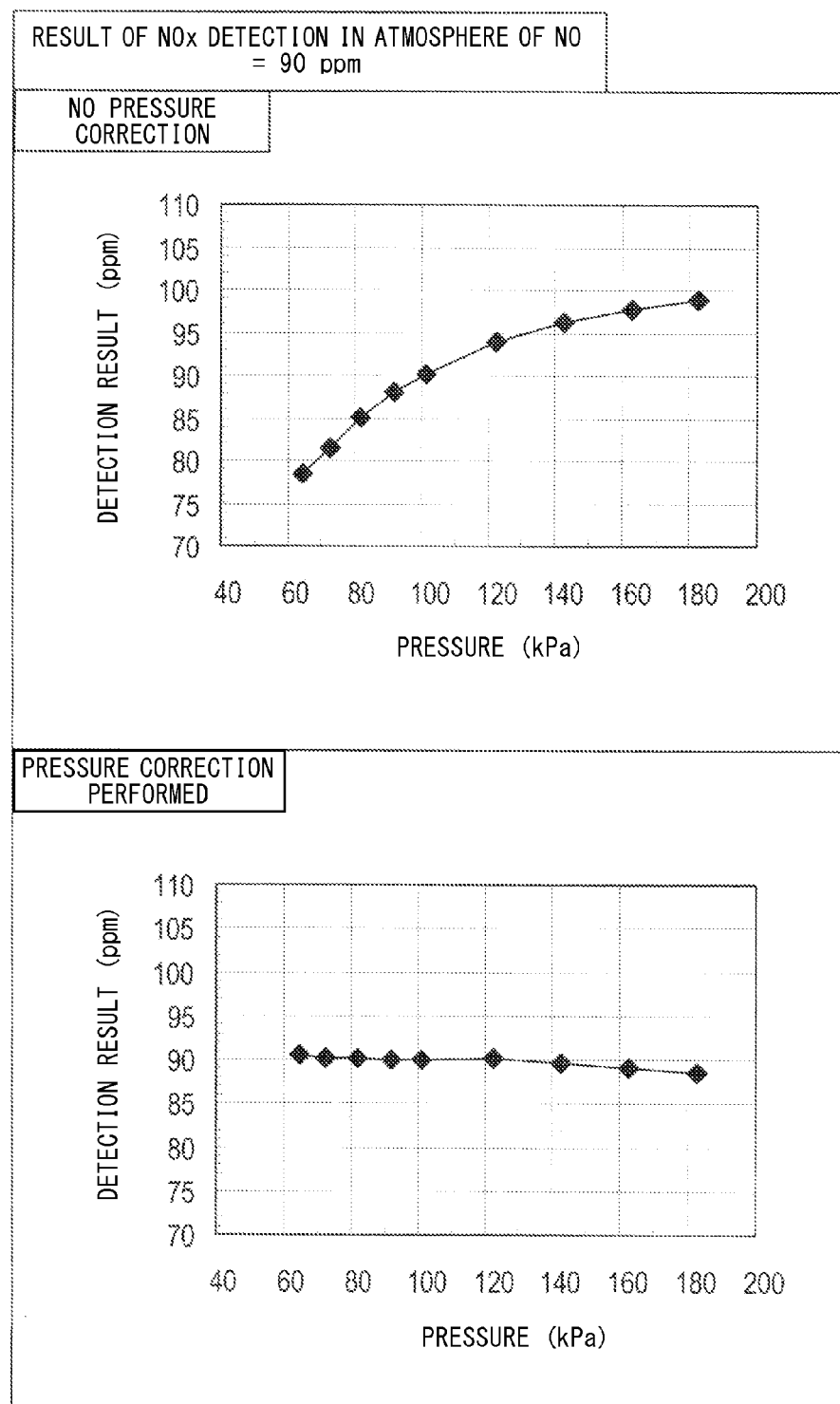
FIG. 9 are graphs showing the results of $NO_x$ concentration detection by the conventional $NO_x$ detection apparatus when the $NO_x$ concentration is 90 ppm.

FIG. 9 shows the results of detection of the $NO_x$ concentration performed by the conventional $NO_x$ detection apparatus for the case where "pressure correction is not preformed" and the case where "pressure correction is performed." In this test, only NO gas was used, and the $NO_x$ concentration was set to 90 ppm.

Notably, the $NO_x$ concentration corrected by the conventional $NO_x$ detection apparatus refers to the $NO_x$ concentration corrected by use of only the above-described Equation 2. Namely, the $NO_x$ concentration corrected by the conventional $NO_x$ detection apparatus refers to the $NO_x$ concentration corrected without reflecting the effect of Equation 3 which is substituted into the above-described Equation 1.

As can be understood from FIG. 9, which shows the detection result for the case where the $NO_x$ concentration is 90 ppm, when "pressure correction is not performed," the detection result changes with a change in pressure. In contrast, when "pressure correction is performed" by use of pressure correction information, the detection result becomes approximately 90 ppm irrespective of the change in pressure. This demonstrates that a decrease in gas detection accuracy can be suppressed.

Notably, when the $NO_x$ concentration is 90 ppm, the $NO_x$ detection apparatus 10 of the present embodiment provides a detection result similar to the detection result provided by the conventional $NO_x$ detection apparatus for the case where "pressure correction is performed" (see the graph on the lower side of FIG. 9). Accordingly, the result of detection of the $NO_x$ concentration by the $NO_x$ detection apparatus 10 of the present embodiment becomes approximately 90 ppm irrespective of a change in the pressure of the to-be-measured gas. In other words, even in the case where the $NO_x$ concentration is 90 ppm, the $NO_x$ detection apparatus 10 of the present embodiment can suppress the influence of a change in the pressure of the to-be-measured gas, to thereby suppress a decrease in gas detection accuracy.

That is, the $NO_x$ detection apparatus 10 of the present embodiment can detect the $NO_x$ concentration while suppressing the influence of the output variation caused by a change in the pressure of the to-be-measured gas in each of the case where the $NO_x$ concentration is 90 ppm and the case where the $NO_x$ concentration is 1500 ppm.

Next, in a second comparative measurement, a sensor output drop ratio obtained before correction by the above-described Equation 5 (correction equation for specific concentration) and a sensor output drop ratio obtained after correction by the Equation 5 were measured in a state in which the $NO_x$ concentration was changed with the pressure of the to-be-measured gas maintained constant.

Notably, in the second comparative measurement, a gas containing NO (0-1500 ppm), $H_2O$ (4%), $O_2$ (7%), and $N_2$ (balance) was used as a sample gas. This measurement was conducted for 55 $NO_x$ sensors. Further, the sensor output drop ratio is calculated by use of the following method. First, the actual $NO_x$ concentration (hereinafter also referred to as the $NO_x$ actual concentration) is subtracted from the detected $NO_x$ concentration so as to calculate a difference value, and then the ratio [%] of the difference value to the $NO_x$ actual concentration is calculated as the sensor output drop ratio.

Figure 7:
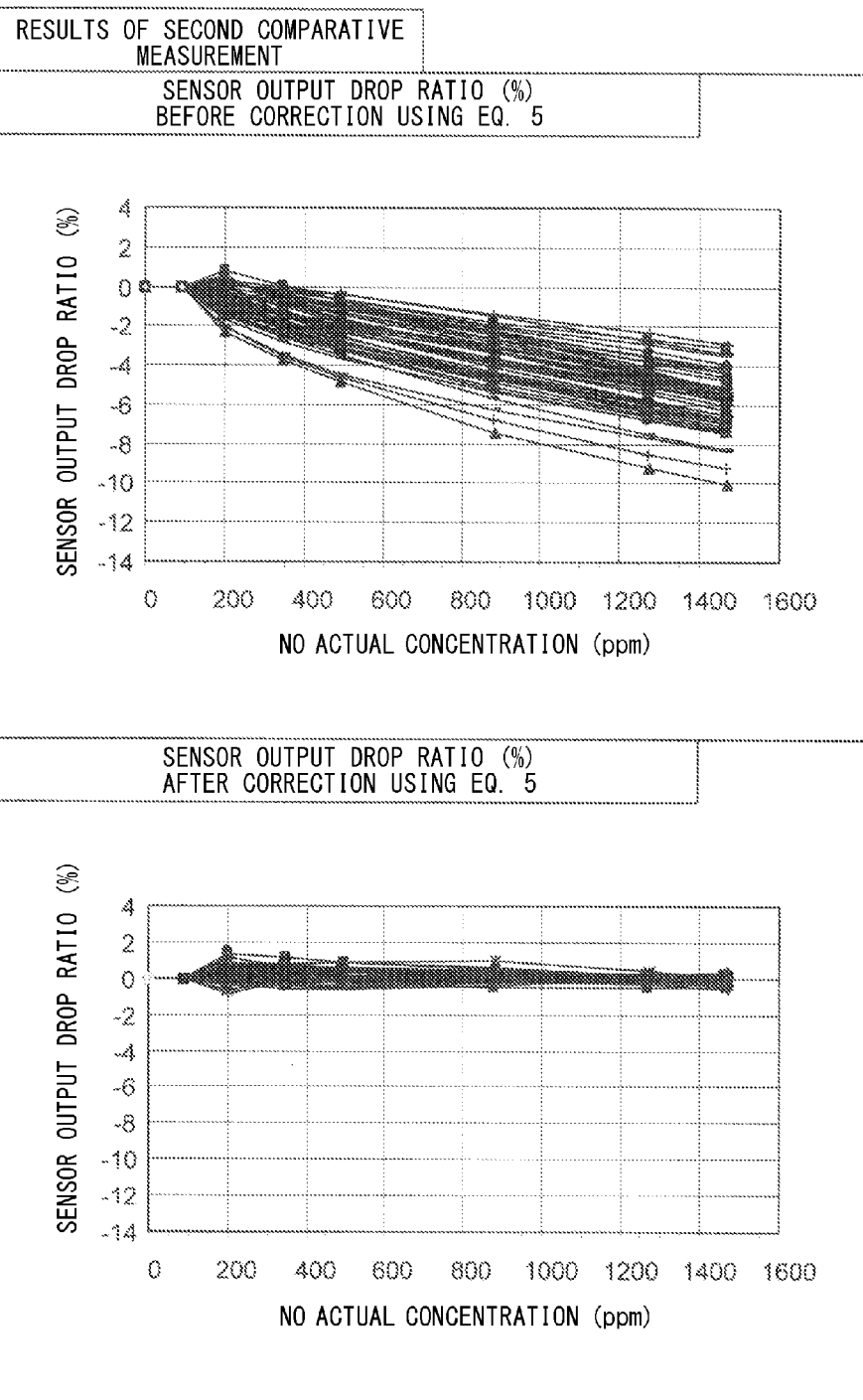
FIG. 7 includes graphs showing the results of a second comparative measurement.
Figure 8:
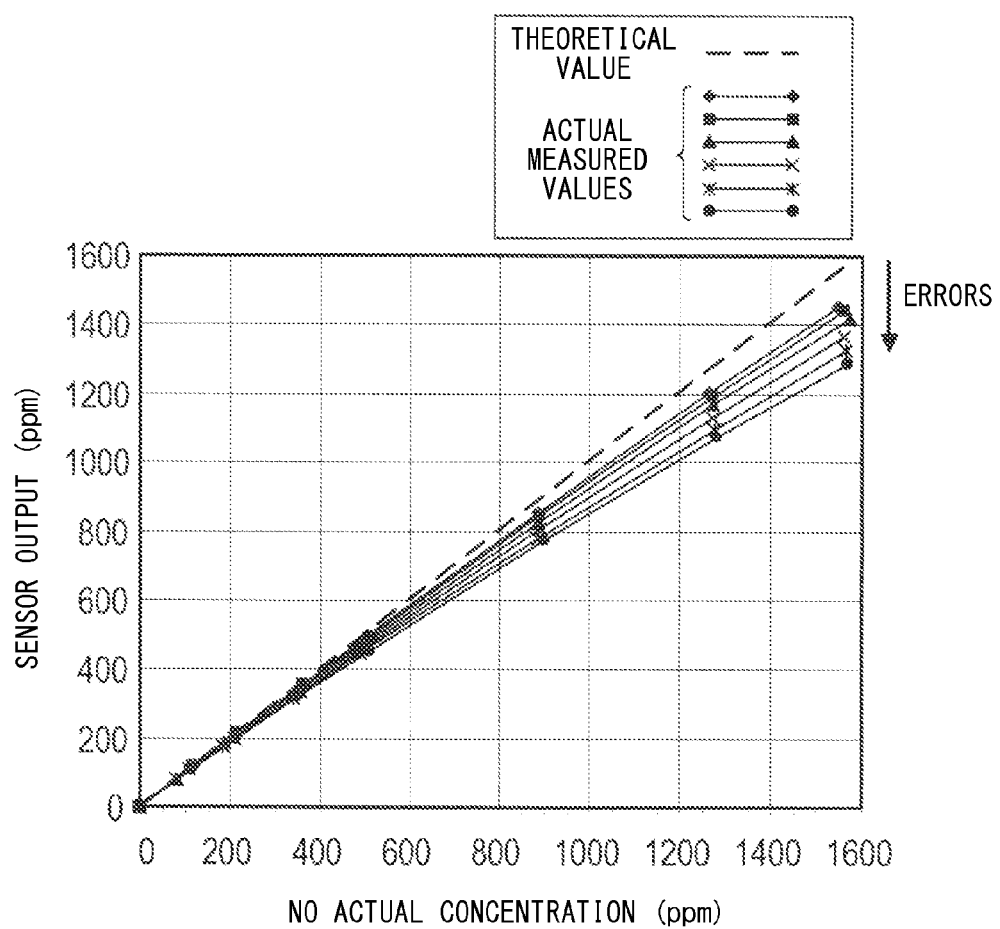
FIG. 8 is a graph showing the relation between actual $NO_x$ concentration and $NO_x$ sensor output for the case where a conventional $NO_x$ detection apparatus is used, wherein a broken line represents a theoretical value and each of six solid lines represents an actual measured value.

FIG. 7 shows results of the second comparative measurements.

The graph on the upper side of FIG. 7 shows the sensor output drop ratios of the 55 $NO_x$ sensors before the correction by Equation 5. This graph shows that, in a range in which the $NO_x$ actual concentration is equal to or higher than 200 ppm, the absolute value of the sensor output drop ratio exceeds 0.2% in at least one of the $NO_x$ sensors. This graph also shows that the difference (error) between the detected $NO_x$ concentration and the $NO_x$ actual concentration increases with the $NO_x$ actual concentration.

The graph on the lower side of FIG. 7 shows the sensor output drop ratios of the 55 $NO_x$ sensors after the correction by Equation 5. This graph shows that the absolute value of the sensor output drop ratio becomes smaller than 0.2% in all the $NO_x$ sensors. This graph also shows that the difference (error) between the detected $NO_x$ concentration and the $NO_x$ actual concentration is small irrespective of the change in the $NO_x$ actual concentration.

As seen from the above, by means of performing correction by use of Equation 5, the difference between the detected $NO_x$ concentration and the $NO_x$ actual concentration can be rendered small even in the concentration range where the $NO_x$ actual concentration exceeds 200 ppm.

1-6. Effects

As described above, the $NO_x$ detection apparatus (or the $NO_x$ sensor system 1) of the present embodiment does not always perform the correction processing (the correction processing performed by use of Equation 5) of step S18, but it determines whether to perform the correction processing of step S18 in accordance with the result of determination performed in step S14.

That is, in the case where the first $NO_x$ concentration $NO_{xpo}$ calculated from the second pumping current Ip2 is higher than a specific concentration (90 ppm or higher), the $NO_x$ detection apparatus 10 of the present embodiment performs the correction processing of step S18. In the case where the first $NO_x$ concentration $NO_{xpo}$ calculated from the second pumping current Ip2 is lower than the specific concentration, the $NO_x$ detection apparatus 10 of the present embodiment does not perform the correction processing of step S18.

The first $NO_x$ concentration $NO_{xpo}$ calculated from the second pumping current Ip2 changes with the actual $NO_x$ concentration. Therefore, the $NO_x$ detection apparatus 10 can determine whether to correct the first $NO_x$ concentration $NO_{xpo}$ in step S18 in accordance with the actual $NO_x$ concentration.

Hence, the $NO_x$ detection apparatus 10 of the present embodiment can suppress a decrease in gas detection accuracy even in the case where an error is involved in the gas detection value based on the sensor output when the $NO_x$ concentration is higher than a specific concentration (90 ppm or higher).

As can be seen from the above-described results of the second comparative measurement shown in FIG. 7, in the present embodiment, the first $NO_x$ concentration $NO_{xpo}$ is corrected to a greater value through performance of the correction processing (the correction processing performed by use of Equation 5) of step S18.

That is, in the case where as shown in the upper graph of FIG. 7 the first $NO_x$ concentration has a tendency to become smaller than the actual $NO_x$ concentration when the $NO_x$ concentration increases, the first $NO_x$ concentration $NO_{xpo}$ is corrected to a greater value through performance of, for example, the correction processing of step S18. Thus, it becomes possible to reduce an error involved in the gas detection value as shown in the lower graph of FIG. 7, to thereby suppress a decrease in the detection accuracy. Notably, when the $NO_x$ concentration increases, the first $NO_x$ concentration becomes smaller than the actual $NO_x$ concentration because of the following reason. When oxygen is pumped out from the first measurement chamber 150 by means of the first pumping cell 110, simultaneously, $NO_x$ within the first measurement chamber 150 is slightly dissociated, and oxygen produced as a result of the dissociation is pumped out from the first measurement chamber 150.

In the present embodiment, in the processing of step S13, the first $NO_x$ concentration $NO_{xpo}$ is calculated by use of a liner function whose input value is the second pumping current Ip2 and whose output value is the first $NO_x$ concentration $NO_{xpo}$.

In the case where the first $NO_x$ concentration $NO_{xpo}$ is calculated by use of the linear function whose input value is the second pumping current Ip2, the amount of increase in the second pumping current Ip2 corresponding to the amount of increase in the $NO_x$ concentration may decrease with an increase in the $NO_x$ concentration.

In contrast, Equation 5 used in the correction processing of step S18 is a higher-order function (quadratic function) whose input value is the first $NO_x$ concentration $NO_{xpo}$ before correction and whose output value is the first $NO_x$ concentration $NO_{xpo}$ after correction.

That is, by means of correcting the first $NO_x$ concentration $NO_{xpo}$ by use of Equation 5 which is a higher-order function (a quadratic function), the amount of increase in the second pumping current Ip2 corresponding to the amount of increase in the $NO_x$ concentration can be increased. Thus, by performing the correction processing of step S18, there can be reduced the error involved in the value of the first $NO_x$ concentration $NO_{xpo}$ which is caused by a decrease in the amount of increase in the second pumping current Ip2.

Thus, even in the case where the amount of increase in the second pumping current Ip2 corresponding to the amount of increase in the $NO_x$ concentration decreases with the increase in the $NO_x$ concentration, the $NO_x$ detection apparatus 10 of the present embodiment can reduce the error involved in the value of the first $NO_x$ concentration $NO_{xpo}$, to thereby suppress a decrease in gas detection accuracy.

Further, the $NO_x$ detection apparatus 10 of the present embodiment calculates the second $NO_x$ concentration $NO_{xp}$ on the basis of the second pumping current Ip2 in step S12, corrects the calculated second $NO_x$ concentration $NO_{xp}$ on the basis of the pressure variation correction information ($K_1$), and uses the corrected second $NO_x$ concentration $NO_{xp}$ as the first $NO_x$ concentration $NO_{xpo}$. Thus, in step S14, the $NO_x$ detection apparatus 10 of the present embodiment can determine whether to correct the first $NO_x$ concentration $NO_{xpo}$ by use of the first $NO_x$ concentration $NO_{xpo}$ in which the result of correction by the pressure variation correction information ($K_1$) has been reflected. Therefore, a decrease in gas detection accuracy can be suppressed more satisfactorily.

1-7. Correspondence Relation Between Terms Appearing in the Description of the Present Embodiment and Terms Appearing in Claims Here, there will be described a correspondence relation between terms appearing in the description of the present embodiment and terms appearing in claims.

The inside first pumping electrode 113 and the outside first pumping electrode 112 correspond to an example of the "paired first electrodes," the inside second pumping electrode 133 and the counterpart second pumping electrode 132 correspond to an example of the "paired second electrodes," and the second measurement chamber 160 corresponds to an example of the $NO_x$ measurement chamber.

The microcomputer 60 which executes steps S12 and S13 corresponds to an example of the first concentration computation means, the microcomputer 60 which executes step S14 corresponds to an example of the specific concentration determination means, and the microcomputer 60 which executes step S18 corresponds to an example of the concentration correction means.

The linear function (y=Ax+B) used in step S12 corresponds to an example of the linear function, and Equation 5 used in step S18 corresponds to an example of the high-order function.

2. Second Embodiment

In the above-described first embodiment, values of coefficients α, β, and γ of Equation 5 are stored in the semiconductor memory 181 of each $NO_x$ sensor before the $NO_x$ detection apparatus is shipped out. However, the values of the coefficients α, β, and γ of Equation 5 may be set through computation processing performed by the microcomputer 60.

Hereinafter, there will be described a second embodiment in which the values of the coefficients of α, β, and γ of Equation 5 are set through computation processing performed by the microcomputer 60. Notably, the second embodiment will be described focusing on differences from the first embodiment. The components of the second embodiment, which are the same as those of the first embodiment, are identified by the same symbols as those used to identify the corresponding components of the first embodiment.

In the $NO_x$ sensor control apparatus 10 of the second embodiment, the second pumping current Ip2 which is detected by use of a gas for determination under a known gas concentration is stored in the semiconductor memory 181 of each $NO_x$ sensor, and the map data shown in FIG. 5 is stored in ROM 63. Notably, in the present second embodiment, before the $NO_x$ sensor 100 is shipped out, the second pumping current IP2 is detected in a state in which the $NO_x$ concentration is 1500 ppm, and the detected second pumping current IP2 is stored in the semiconductor memory 181.

Next, in step S4 of the concentration detection processing routine, the $NO_x$ sensor control apparatus of the second embodiment performs processing of setting the values of coefficients of α, β, and γ of Equation 5 in addition to processing of acquiring the $NO_x$ pressure correction coefficient ($k_1$) from the semiconductor memory 181.

Namely, in step S4, the microcomputer 60 first accesses the semiconductor memory 181 so as to acquire the previously stored second pumping current Ip2, and calculates the $NO_x$ concentration equivalent value from the second pumping current Ip2. Next, the microcomputer 60 calculates the difference (output drop ratio [%]) between the calculated $NO_x$ concentration equivalent value and the known gas concentration, and determines the values of the coefficients α, β, and γ are on the basis of the "output drop ratio" and the "map data sets (shown in FIG. 5) read out from ROM 63."

Next, in step S18, the microcomputer 60 corrects the first $NO_x$ concentration $NO_{xpo}$ ($NO_x$ concentration equivalent value) by use of Equation 5 determined by the coefficients α, β, and γ set in step S4.

In this manner, the $NO_x$ sensor control apparatus 10 of the second embodiment sets the values of the coefficients α, β, and γ of Equation 5 on the basis of the second pumping current which is output when the $NO_x$ concentration is 1500 ppm.

Since the second pumping current Ip2 output from the $NO_x$ sensor 100 represents a value in which the individual difference of the $NO_x$ sensor 100 is reflected, Equation 5 can be appropriately set in accordance with the individual difference of the $NO_x$ sensor 100 by setting the values of the coefficients α, β, and γ of Equation 5 on the basis of the second pumping current Ip2 which is output when the $NO_x$ concentration is 1500 ppm.

Further, by means of previously preparing map data sets for computing the coefficients α, β, and γ (as shown in FIG. 5), Equation 5 can be appropriately set in accordance with the individual difference of the $NO_x$ sensor 100 by detecting only the second pumping current Ip2 which is output when the $NO_x$ concentration is 1500 ppm without detecting the second pumping current Ip2 over a wide range of $NO_x$ concentration.

Here, there is described a correspondence relation between a term appearing in the description of the present embodiment and a term appearing in a claim. The microcomputer 60 which executes step S4 corresponds to an example of the correction information setting means.

3. Other Embodiments

The embodiments of the present invention have been described above. However, the present invention is not limited to the above-described embodiments, and various modifications are possible without departing from the scope of the present invention.

For example, in the above-described embodiments, a "concentration range of 90 ppm or higher" is set as a specific concentration range used in step S14. However, the specific concentration range used in step S14 is not limited to this range, and an arbitrary concentration range may be set in accordance with the characteristic of the $NO_x$ sensor, the measurement environment, or the like.

The correction method employed in step S18 is not limited to a method performed through use of a function such as Equation 5, and another method for correcting the $NO_x$ concentration (e.g., a method for correcting the $NO_x$ concentration by using a map which represents a correlation between the $NO_x$ concentration before correction and the $NO_x$ concentration after correction) may be used.

The correction method employed in step S22 is not limited to a method performed through use of functions such as Equations 1 to 3, and another method for correcting the $NO_x$ concentration (e.g., a method for correcting the $NO_x$ concentration by using a map in which a correction amount is assigned to each of pressure ranges) may be used.

The map data sets used for computing the coefficients a and b in steps S16 and S20 are not limited to those shown in FIG. 4, and arbitrary map data sets may be used in accordance with the characteristic of the $NO_x$ sensor, the measurement environment, or the like. Similarly, the map data sets used for computing coefficients α, β, and γ in step S18 are not limited to those shown in FIG. 5, and arbitrary map data sets may be used in accordance with the characteristic of the $NO_x$ sensor, the measurement environment, or the like.

Meanwhile, in the present embodiments, in step S13, the first $NO_x$ concentration $NO_{xpo}$ ($NO_x$ concentration after pressure correction at pressure Po) is calculated by use of the second $NO_x$ concentration ($NO_x$ concentration before pressure correction) and Equation 2, and then the calculated result is output. Further, in step S22, the corrected $NO_x$ concentration Rno is calculated by use of Equation 1. However, the processing for calculating the corrected $NO_x$ concentration Rno is not limited to the above-described processing. For example, step S13 may be omitted. In this case, steps S14 to S20 are executed with the second $NO_x$ concentration NO($NO_x$ concentration before pressure correction) used as the first $NO_x$ concentration, and the corrected $NO_x$ concentration Rno is then calculated by use of Equation 1 into which Equations 2 and 3 has been substituted.

DESCRIPTION OF REFERENCE NUMERALS

10: $NO_x$ sensor control apparatus ($No_x$ detection apparatus)
60: microcomputer
100: $No_x$ sensor
101: $No_x$ sensor element
110: first pumping cell
120: oxygen concentration detection cell
130: second pumping cell
150: first measurement chamber
160: second measurement chamber 181: storage means (semiconductor memory)
200: vehicle-side control apparatus
300: pressure sensor

What is claimed is:

1. An $NO_x$ detection apparatus connected to an $NO_x$ sensor and adapted to detect an $NO_x$ concentration within a to-be-measured gas, the $NO_x$ sensor including a first measurement chamber, a first pumping cell including paired first electrodes positioned internally and externally, respectively, of the first measurement chamber, the first pumping cell adjusting an oxygen concentration of the to-be-measured gas introduced into the first measurement chamber, an $NO_x$ measurement chamber in communication with the first measurement chamber, and a second pumping cell including paired second electrodes positioned internally and externally, respectively, of the $NO_x$ measurement chamber, a second pumping current flowing between the paired second electrodes and corresponding to the $NO_x$ concentration within the to-be-measured gas whose oxygen concentration has been adjusted in the first measurement chamber, the $NO_x$ detection apparatus comprising:
first concentration computation means for computing a first $NO_x$ concentration on the basis of the second pumping current;
specific concentration determination means for determining whether the first $NO_x$ concentration is higher than a predetermined specific concentration; and
concentration correction means for correcting the first $NO_x$ concentration using predetermined specific concentration correction information set for each $NO_x$ sensor in advance, wherein
when the specific concentration determination means determines that the first $NO_x$ concentration is higher than the predetermined specific concentration, the concentration correction means corrects the first $NO_x$ concentration, and
when the specific concentration determination means determines that the first $NO_x$ concentration is not higher than the predetermined specific concentration, the concentration correction means does not correct the first $NO_x$ concentration.

2. The $NO_x$ detection apparatus according to claim 1, wherein the concentration correction means corrects the first $NO_x$ concentration by increasing the first $NO_x$ concentration.

3. The $NO_x$ detection apparatus according to claim 1, wherein
the first concentration computation means computes the first $NO_x$ concentration using a linear function having an input value of the second pumping current and having an output value of the first $NO_x$ concentration; and
the predetermined specific concentration correction information includes a high-order function having an input value of the first $NO_x$ concentration before being corrected and having and output value of the first $NO_x$ concentration after being corrected.

4. The $NO_x$ detection apparatus according to claim 1, wherein the first concentration computation means computes a second $NO_x$ concentration on the basis of the second pumping current, and obtains the first $NO_x$ concentration by correcting the second $NO_x$ concentration on the basis of predetermined pressure variation correction information which is set for the $NO_x$ sensor in advance.

5. The $NO_x$ detection apparatus according to claim 1, further comprising correction information setting means for setting the predetermined specific concentration correction information on the basis of the second pumping current at a predetermined $NO_x$ concentration.

6. An $NO_x$ sensor system comprising:
an $NO_x$ sensor including a first measurement chamber, a first pumping cell including paired first electrodes positioned internally and externally, respectively, of the first measurement chamber and adjusting an oxygen concentration of a to-be-measured gas introduced into the first measurement chamber, an $NO_x$ measurement chamber in communication with the first measurement chamber, and a second pumping cell including paired second electrodes provided internally and externally, respectively, of the $NO_x$ measurement chamber, a second pumping current flowing between the paired second electrodes and corresponding to an $NO_x$ concentration within the to-be-measured gas whose oxygen concentration has been adjusted in the first measurement chamber; and
an $NO_x$ detection apparatus connected to the $NO_x$ sensor and adapted to detect an $NO_x$ concentration within the to-be-measured gas, the $NO_x$ detection apparatus including
first concentration computation means for computing a first $NO_x$ concentration on the basis of the second pumping current;
specific concentration determination means for determining whether the first $NO_x$ concentration is higher than a predetermined specific concentration; and
concentration correction means for correcting the first $NO_x$ concentration using predetermined specific concentration correction information set for the $NO_x$ sensor in advance wherein
when the specific concentration determination means determines that the first $NO_x$ concentration is higher than the predetermined specific concentration, the concentration correction means corrects the first $NO_x$ concentration, and
when the specific concentration determination means determines that the first $NO_x$ concentration is not higher than the predetermined specific concentration, the concentration correction means does not correct the first $NO_x$ concentration.

* * * * *